(12) United States Patent
Rogers

(10) Patent No.: US 8,585,707 B2
(45) Date of Patent: Nov. 19, 2013

(54) CONTINUOUS LOW IRRADIANCE PHOTODYNAMIC THERAPY METHOD

(76) Inventor: Gary S. Rogers, Wenham, MA (US)

(*) Notice: Subject to any disclaimer, the term of this patent is extended or adjusted under 35 U.S.C. 154(b) by 1953 days.

(21) Appl. No.: 11/448,296

(22) Filed: Jun. 7, 2006

(65) Prior Publication Data
US 2007/0288071 A1   Dec. 13, 2007

(51) Int. Cl.
*A61N 5/06* (2006.01)

(52) U.S. Cl.
USPC .................................. 606/88; 606/89; 128/898

(58) Field of Classification Search
USPC ........................................ 128/898; 607/88–94
See application file for complete search history.

(56) References Cited

U.S. PATENT DOCUMENTS

| | | | |
|---|---|---|---|
| 4,761,047 A | 8/1988 | Mori | |
| 4,885,663 A | 12/1989 | Parker | |
| 4,907,132 A | 3/1990 | Parker | |
| 5,042,900 A | 8/1991 | Parker | |
| 5,568,964 A | 10/1996 | Parker et al. | |
| 5,997,569 A | 12/1999 | Chen et al. | |
| 6,030,089 A | 2/2000 | Parker et al. | |
| 6,045,575 A * | 4/2000 | Rosen et al. | 607/88 |
| 6,443,978 B1 * | 9/2002 | Zharov | 607/91 |
| 6,494,900 B1 * | 12/2002 | Salansky et al. | 607/89 |
| 6,573,421 B1 | 6/2003 | Lemaire | |
| 6,596,016 B1 * | 7/2003 | Vreman et al. | 607/88 |
| 6,602,274 B1 * | 8/2003 | Chen | 607/88 |
| 6,676,655 B2 | 1/2004 | McDaniel | |
| 6,723,750 B2 | 4/2004 | Voet | |
| 6,743,249 B1 * | 6/2004 | Alden | 607/88 |
| 6,860,896 B2 * | 3/2005 | Leber et al. | 607/1 |
| 6,897,238 B2 | 5/2005 | Anderson | |
| 2002/0138120 A1 * | 9/2002 | Whitehurst | 607/88 |
| 2003/0114434 A1 * | 6/2003 | Chen et al. | 604/20 |
| 2004/0210276 A1 * | 10/2004 | Altshuler et al. | 607/88 |
| 2004/0215292 A1 * | 10/2004 | Chen | 607/88 |
| 2005/0070977 A1 * | 3/2005 | Molina | 607/88 |

FOREIGN PATENT DOCUMENTS

| | | |
|---|---|---|
| WO | WO 94/06424 | 3/1994 |
| WO | WO 95/07077 | 3/1995 |

OTHER PUBLICATIONS

Bisland, Stuart K. et al., "Metronomic Photodynamic Therapy: A Novel Approach to Treating Brain Tumours," Ontario Cancer Institute and Dept. of Medical Biophysics, U Toronto, presented at OPTO Canada meeting, Ottawa (May 9, 2002).

Bisland, Stuart K. et al., "Metronomic Photodynamic Therapy as a New Paradigm for Photodynamic Therapy: Rationale and Preclinical Evaluation of Technical Feasibility for Treating Malignant Brain Tumors," Photchem. & Photobiol. (Jul./Aug. 2004).

(Continued)

*Primary Examiner* — David Shay
(74) *Attorney, Agent, or Firm* — Nutter McClennen & Fish LLP

(57) ABSTRACT

Systems and methods are providing for treating a patient with continuous low irradiance photodynamic therapy. A disclosed method includes applying a photosensitizer to the patient; applying a conformable skin facing light applicator to the patient; and providing continuous low irradiance photodynamic therapy through the light applicator. A disclosed system includes a light applicator having a fiber optic cloth. The light applicator is conformable so that it can be worn against a patient's skin and the fiber optic cloth has a two dimensional surface that emits light in a direction toward a patient's skin. In this aspect, the power of the light emitted from the two dimensional surface in a direction toward a patient's skin is less than or equal to about 5 mW/cm$^2$.

16 Claims, 5 Drawing Sheets

(56) References Cited

OTHER PUBLICATIONS

Kloek, J. et al., "Prodrugs of 5-Aminolevulinic Acid for Photodynamic Therapy," Photochem. & Photobiol. 64(6):994-1000 (Dec. 1996).

Ladner, D.P. et al., "Photodynamic Diagnosis of Breast Tumours After Oral Application of Aminolevulinic Acid," British J. Cancer 84:33-37 (2001).

PCT Search Report, from corresponding PCT/US07/13475, dated Jun. 18, 2008.

Cuenca, R. et al., "Breast Cancer With Chest Wall Progression: Treatment With Photodynamic Therapy," Annals Surg. Oncology 11(3):322-27 (2004).

Dimofte, A. et al., "In Vivo Light Dosimetry for Motexafin Lutetium-Mediated PDT of Recurrent Breast Cancer," Lasers Surg. Med. 31(5):305-12 (2002).

Loewen, G. et al., "Endobronchial Photodynamic Therapy for Lung Cancer," Lasers Surg. Med. 38:364-70 (2006).

Mackenzie, G. et al., "How Light Dosimetry Influences the Efficacy of Photodynamic Therapy With 5-Aminolaevulinic Acid for Ablation of High-Grade Dysplasia in Barrett's Esophagus," Lasers Med. Sci. 23:203-10 (2008).

Moghissi, K. et al., "The Place of Bronchoscopic Photodynamic Therapy in Advanced Unresectable Lung Cancer: Experience of 100 Cases," Eur J. Cardio-Thoracic Surg. 15:1-6 (1999).

Pinthus, J. et al., "Photodynamic Therapy for Urological Malignancies: Past to Current Approaches," J. Urology 175:1201-07 (Apr. 2006).

Taber, S. et al., "Photodynamic Therapy for Palliation of Chest Wall Recurrence in Patients With Breast Cancer," J. Surgical Oncology 68:209-14 (1998).

Thong, P.S. et al., "Immune Response Against Angiosarcoma Following Lower Fluence Rate Clinical Photodynamic Therapy," J. Environ. Pathol. Toxicol. Oncol. 27(1):35-42 (2008).

Trachtenberg, J. et al., "Vascular Targeted Photodynamic Therapy With Palladium-Bacteriopheophorbide Photosensitizer for Recurrent Prostate Cancer Following Definitive Radiation Therapy: Assessment of Safety and Treatment Response," J. Urology 178:1974-79 (2007).

Wolfsen, H. et al., "Photodyanamic Therapy for Dysplastic Barrett Esophagus and Early Esophageal Adenocarcinoma," Mayo Clinic Proc. 77:1176-81 (2002).

Chinese Office Action issued May 18, 2011 for Application No. 200780021159.X (12 Pages).

Han et al., Impact of laser power density on retinal and choroidal biological effect during HMME-PDT. Chin J Laser Med Surg. Apr. 2006;15(2):89-92.

International Report on Patentability for Application No. PCT/US2007/013475 mailed Dec. 24, 2008 (7 pages).

\* cited by examiner

CONTINUOUS LOW IRRADIANCE PHOTODYNAMIC THERAPY METHOD

BACKGROUND OF THE INVENTION

Photodynamic therapy (PDT) is a ternary treatment for cancer involving three key components: a photosensitizer drug, light, and tissue oxygen. It is also being used for treatment of psoriasis and acne, among other skin growths and is an approved treatment for wet macular degeneration.

In photodynamic therapy, either a photosensitizer or the metabolic precursor of one is administered to the patient. A photosensitizer is a chemical compound that can be excited by light of a specific wavelength. This excitation uses visible or near-infrared light. The tissue to be treated is exposed to light suitable for exciting the photosensitizer. Usually, the photosensitizer is excited from a ground singlet state to an excited singlet state. It then undergoes intersystem crossing to a longer-lived excited triplet state. One of the few chemical species present in tissue with a ground triplet state is molecular oxygen. When the photosensitizer and an oxygen molecule are in close proximity, an energy transfer can take place that allows the photosensitizer to relax to its ground singlet state, and create an excited singlet state oxygen molecule. Singlet oxygen is a very aggressive chemical species and will very rapidly react with any nearby biomolecules. (The specific targets depend heavily on the photosensitizer chosen.) Ultimately, these destructive reactions will result in cell killing through apoptosis or necrosis.

Photodynamic therapy is delivered as an acute therapy comprising a single drug and light administration, or in a series of administrations over time (usually with months between PDT sessions). More recently, the concept of metronomic PDT ("mPDT") has been introduced. In mPDT, the drug and/or light are delivered either in multiple pulses or continuously such that the 'fractions' overlap pharmacokinetically and photobiologically. (See, e.g., Stuart K. Bisland et al., "Metronomic photodynamic therapy: A novel approach to treating brain tumours," Ontario Cancer Institute and Dept. of Medical Biophysics, University of Toronto, presented at the OPTO Canada meeting in Ottawa; 9 May 2002; and Stuart K. Bisland et al., "Metronomic Photodynamic Therapy as a New Paradigm for Photodynamic Therapy: Rationale and Preclinical Evaluation of Technical Feasibility for Treating Malignant Brain Tumors," Photochemistry and Photobiology (July/August 2004), each of which is incorporated by reference in its entirety).

Despite these advances however, at least two important challenges remain in providing effective low dose therapy: (1) delivery of light to the target tissue over an extended period in a manner that provides consistent energy delivery to what can be an uneven surface contour; and (2) delivery of light to the target tissue over an extended period in a manner that will be acceptable to patients over this time.

BRIEF SUMMARY OF THE INVENTION

The present invention is directed to systems and methods for providing continuous low irradiance photodynamic therapy to a patient. The methods and systems of the invention are most likely to be applicable to patients with conditions that may be amenable to treatment using conventional photodynamic therapy, but the invention enables treatments that are less damaging to the patient and that may be provided in ways that can be comfortable and convenient for the patient. In one aspect, the invention includes a method for providing continuous low irradiance photodynamic therapy to a patient. The method includes applying a photosensitizer to the patient; applying a conformable skin facing light applicator to the patient; and providing continuous low irradiance photodynamic therapy through the light applicator.

In specific embodiments of this aspect of the invention, the light applicator can include a fiber optic cloth and the light applicator can provide a light intensity to the patient of less than or equal to about 5 mW/cm$^2$. Embodiments of the method of this aspect can also include, for example, 5-aminolevulinic acid as the photosensitizer, and the photosensitizer can be administered orally. In still further specific embodiments, the method can be applied to treat a disease of the skin, a skin or soft tissue cancer, skin metastases of a malignant melanoma or chest wall progression of breast cancer in the patient, or small joint arthritis.

In a further aspect, the invention includes a system for providing continuous low irradiance photodynamic therapy. The system includes a light applicator having a fiber optic cloth. The light applicator is conformable so that it can be worn against a patient's skin and the fiber optic cloth has a two dimensional surface that emits light in a direction toward a patient's skin. In this aspect, the power of the light emitted from the two dimensional surface in a direction toward a patient's skin is less than or equal to about 5 mW/cm$^2$.

In further specific embodiments of the various aspects of the invention, the light applicator can provide a light intensity to the patient of between about 0.25 and 3 mW/cm$^2$. The light applicator can also be applied to the patient continuously for a period of greater than or equal to about four, 12 or 24 hours. The light applicator can also have an effective treatment area of greater than or equal to 10 cm$^2$, or greater than or equal to 100 cm$^2$.

In still further embodiments, the light applicator can include two surface areas for treating two areas of the patient's skin. The two surface areas can provide light of differing intensity or light of differing wavelengths. Systems of, or used by, the invention may also include at least one sensor provided in communication with a controller for measuring at least one of skin temperature, oxygen saturation in tissue being treated, and photosensitizer drug level. The controller can use information provided by the sensor to turn on or off the power to the light applicator or to vary the fluence provided by the light applicator. Where the light applicator includes two surface areas for treating two areas of the patient's skin, at least one sensor can associated with the treatment provided at each surface area.

Still further, the light applicator can also be integrated into a garment that is worn by the patient. The light applicator may be affixed to the garment, affixed with an adhesive, affixed by stitching, or, the garment may consist essentially of the light applicator. The light applicator can further be configured to be affixed to the patient's skin. For example, the light applicator might be fixed to the patient's skin using an adhesive, or it may include a backing fixed to a back side of the fiber optic cloth, the backing being larger than the fiber optic cloth and having adhesive on a skin facing surface area for affixing the light applicator to a patient's skin.

BRIEF DESCRIPTION OF THE DRAWINGS

The invention will be more fully understood from the following detailed description taken in conjunction with the accompanying drawings.

DETAILED DESCRIPTION OF THE INVENTION

The present invention enables the use of continuous low irradiance photodynamic therapy. Using the methods and systems described herein, it may be possible to treat patients outside of the clinic, in a way that can be home based and unobtrusive to the patient. The methods and systems of the invention are most likely to be applicable to patients with cutaneous, subcutaneous, mucosal, intra-articular, and hematologic diseases that may be amenable to treatment using photodynamic therapy. These include patients having skin and soft-tissue cancers, acne, breast cancer, and in particular, patients having metastatic lesions through the dermis/epidermis and subcutaneous and breast fat and certain lymphomas.

Figure 1:
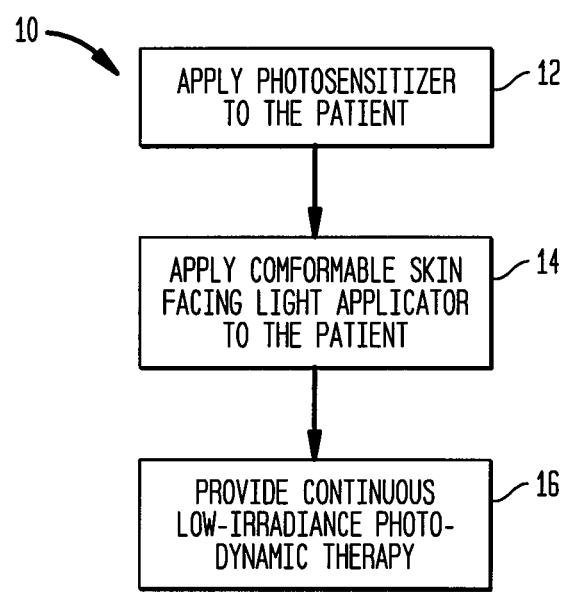
FIG. 1 illustrates a flow of method steps according to one embodiment of the invention providing continuous low irradiance photodynamic therapy.

A method 10 according to one embodiment of the invention is illustrated in FIG. 1. According to the method 10, a photosensitizer is applied to the patient to be treated 12. A variety of photosensitizers are known in the art and can be used with the invention. The photosensitizer can be applied topically to the treatment site, post-operatively, intra-muscularly, intra-articularly, intra-veinously, or orally at a specified time or times prior or during treatment. Conventional photosensitizers may be used (including those described in the documents incorporated by reference in the Background), or others may be developed specifically for use with the invention.

In one exemplary embodiment, the photosensitizer is 5-aminolevulinic acid (ALA). 5-Aminolevulinic acid, also known as 5-aminolaevulinic acid, delta-aminolevulinic acid, delta-aminolaevulinic acid, or 5-amino4-oxopentanoic acid, is an intermediate in the pathway to the production of the photosensitizer, proptoporphyrin IX (PpIX). In the present invention, 5-Aminolevulinic acid can be used as a salt, such as the hydrochloride salt. 5-Aminolevulinic acid can also be used in a pharmacologically equivalent form, such as an amide or ester. Examples of precursors and products of 5-aminolevulinic acid and pharmacologically equivalent forms of 5-aminolevulinic acid that can be used in the present invention are described in J. Kloek et al., "Prodrugs of 5-Aminolevulinic Acid for Photodynamic Therapy," Photochemistry and Photobiology, Vol. 64 No. 6, pp. 994-1000 (December 1996); WO 95/07077, published Mar. 16, 1995, entitled Photochemotherapeutic Compositions Containing 5-Aminolevulinic Acid; Q. Peng et al., "Build-Up of Esterified Aminolevulinic-Acid-Derivative-Induced Porphyrin Fluorescence in Normal Mouse Skin," Journal of Photochemistry and Photobiology B: Biology, Vol. 34, No. 1, (June 1996); and WO 94/06424, Mar. 31, 1994, entitled Transcutaneous In Vivo Activation of Photosensitive Agents in Blood. These references are incorporated herein in their entirety. The term "ALA" refers to all of the above-referenced compounds as described herein.

In one preferred embodiment, ALA is provided oral administration. Oral application of ALA in the context of breast cancer is described, for example, in D. P. Ladner et al., "Photodynamic diagnosis of breast tumours after oral application of aminolevulinic acid," British Journal of Cancer, Vol. 84, pp. 33-37 (2001), which is incorporated herein in its entirety. By providing the photosynthesizer in an orally administered form, treatments may more readily be provided on an outpatient or even an at-home basis.

In further embodiments, Photofrin (available from Axcan Pharma Ltd. of Ireland) can be intravenously administered as the photosensitizing agent. This drug has been FDA approved for PDT treatment of endobronchial lung and esophageal cancers, and also has been approved for the treatment of bladder cancer in Canada. Due to the Photofrin's extended half-life, the level of drug in the tissue remains stable for over 36 hours after intravenous administration. In addition, there are more than fifteen photosensitizers described, for example, in the U.S. patents and patent applications that could find suitable use with the present invention.

Method 10 further includes applying a conformable, skin-facing light applicator to the patient 14. The applicator should be conformable so that its shape can adapt to the contours of the patient's skin and so that the applicator is comfortable for the patient over an extended period of application. The applicator must be skin facing in the sense that it must irradiate the skin. The applicator will preferably be in contact with the patient's skin, or very close to the patient's skin, in use. Specific examples of fiber optic cloth based applicators are described in greater detail below.

Treatment of the patient by providing continuous low-irradiance photodynamic therapy 16 is further included in method 10. Low irradiance treatment generally provides a treatment level that is sufficient to initiate a photodynamic effect, which can then be continued over a desired period of time to achieve the desired treatment level in the target tissue, without causing damage to surrounding tissue. This is particularly the case where the surrounding tissue has already been damaged or is susceptible to damage due to prior treatments. In one preferred embodiment, low irradiance treatment includes providing a light intensity to the skin that is less than or equal to about 5 mW/cm$^2$, or more preferably, between about 0.25 and 3 mW/cm$^2$. In order to achieve the desired light fluence in the target tissue, the applicator is preferably applied in dosages of greater than about one hour, greater than about four hours, greater than about 12 hours, or greater than or equal to about 24 hours. Treatments may also be fractionated—, i.e., multiple doses of, say, 12 hours each, may be provided. Still further, the light source, or segments of the light source, can be independently turned on and off automatically (for example, in response to readings from a sensor on the patient that indicates that tissue in a particular area is oxygen depleted).

Figure 2:
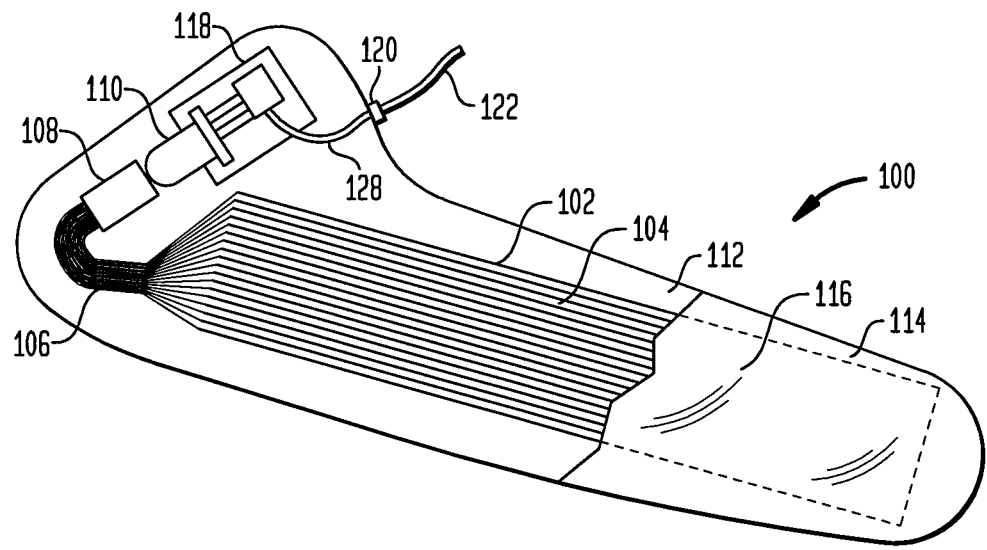
FIG. 2 illustrates a light applicator of the invention useful with the method of FIG. 1.

In one exemplary embodiment illustrated in FIG. 2, a light applicator 100 is formed from a fiber optic cloth 102 having a number of optical fibers 104 that "leak" light out of at least one surface of the cloth at a known, and controllable, rate. The optical fibers 104 are gathered at one end to form a fiber optic cable 106 leading to a connector 108 where a light source 110 can be applied to power the fiber optic cloth 102. In another embodiment, the light applicator can be formed of an array of light emitting diodes fixed to a conformable substrate such as a plastic film or a cloth.

Fiber optic cloth 102 can be provided on a backing layer 112 to facilitate its application to a patient's skin. The backing layer 112 can be, for example, a film or coating that can be applied to a back side of the fiber optic cloth, or it could be a portion of the patient's clothing to which a transparent layer 114 has been applied to form a pocket having a transparent window 116 that can be directed toward the patient's skin.

Light source 110 is mounted to a holder 118 that, in turn, is mounted to the backing layer 112. In this way, a desired connection between the light source 110 and the connector 108 can be maintained even if the light applicator 100 is jostled or moved. Wiring 128 for the light source 110 can lead to an electrical connector 120, and a cable 122 can be attached to the connector so that the light source can be electrically connected to a source of power and any desired control electronics that can be provided "off-board." Alternatively, a power source, such as a battery, can be provided on the backing layer 112 for connection to wiring 118 to power the light source.

Light source 110 can be a commercially available laser or LED light source, and preferably emits light in a wavelength in the visible range. More preferably, the light source can produce light having a wavelength between about 300 and 700 nm, still more preferably, the light source can produce light having a wavelength between about 550 and 650 nm. In one embodiment, the light source can be a laser producing light having a wavelength of about 630 nm, as such light sources are used in consumer electronic applications and can be found in small, light weight, low cost packages.

Figure 3:
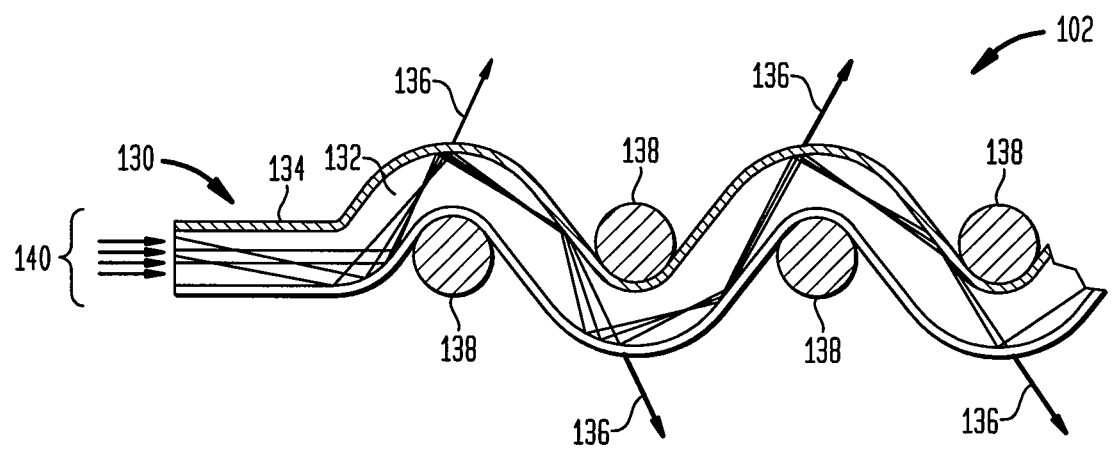
FIG. 3 illustrates a portion of the light application of FIG. 2.

Further details of one embodiment of fiber optic cloth 102 can be seen in FIG. 3, which shows a portion of one optical fiber 130 from cloth 102. The optical fiber 130 can include a light transmitting core 132 of a suitable transparent material and an outer sheath or cladding 134 of a second transparent material typically having a lower index of refraction than the core material to regulate the amount of light 136 that escapes from the fiber 130 along its length. In the illustrated embodiment, the optical fiber 130 is woven about fill threads 138 to create a cloth that is comfortable and conformable, and also to create bends in the fiber that allow light to escape the fiber. The amount of light emitted by the cloth will depend on the depth and frequency of these bends, and also upon the nature of the light input 140 to the fiber. Fiber optic cloth having this construction can be seen in U.S. Pat. Nos. 6,030,089; 5,568, 964; 4,885,663; 4,907,132; and 5,042,900; each of which is hereby incorporated by reference.

Alternatively, optical fiber 130 could rely on disruptions on the external surface of the optical fibers, by scratching, etching or otherwise causing mechanical, chemical or other deformations at discrete locations along their lengths. Examples of such fibers and their use are provided in U.S. Pat. Nos. 4,885, 663 and 4,761,047, which are hereby incorporated by reference. One possible advantage of this approach to forming the fiber optic cloth 102 is that the fibers can readily be designed to emit light on only one side, i.e., the patient facing side, so that power supplied to the applicator will more efficiently be applied to treatment.

It is also desirable for the light applicator to cover a sufficient area to provide the desired treatment. In one embodiment, the applicator has an effective treatment area (i.e., the surface area that provides light directed towards the patient's skin) of greater than equal to about 10 cm$^2$. In a further embodiment, the applicator has an effective treatment area of greater than or equal to about 100 cm$^2$, or in another embodiment, an effective treatment area of about 100 cm$^2$.

Figure 4A:
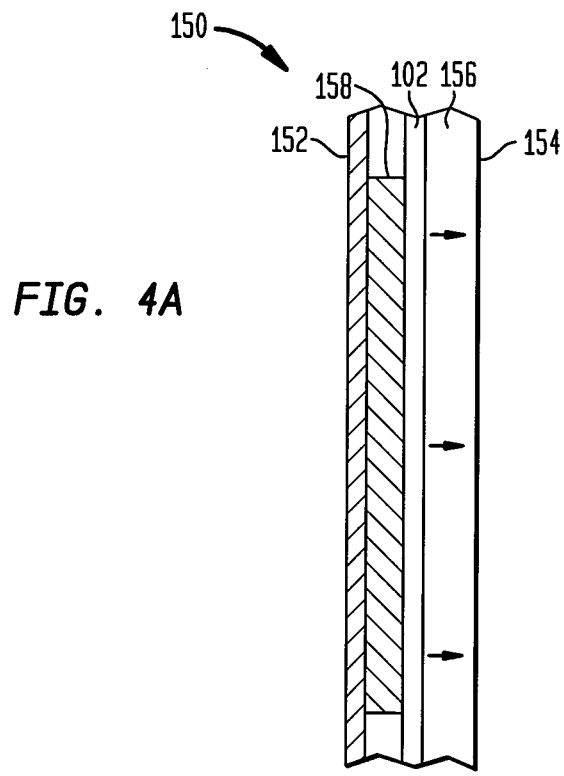
FIGS. 4A and 4B illustrate variations on the configuration of the light applicator of FIG. 2.
Figure 4B:
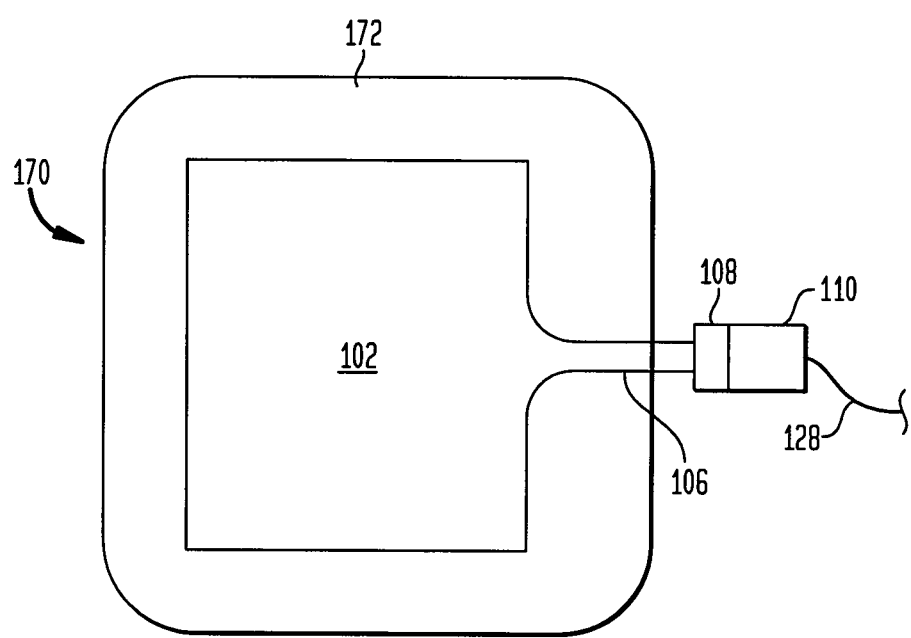

FIGS. 4A and 4B illustrate two further embodiments of a light applicator 150, 170, respectively, that can be used with the present invention. Light applicator 150 applies fiber optic cloth 102 to an article of clothing 152 that is intended to be worn up against the patient's skin 154 so that light 156 emanating from the fiber optic cloth 102. In the illustrated embodiment, an attachment element 158 attaches the fiber optic cloth 102 to the clothing 152. In one embodiment, the attachment element 158 could be a film or backing that is attached to the fiber optic cloth 102 and stitched into the clothing. In another embodiment, attachment element 158 could be a layer of pressure sensitive adhesive that could applied directly to the fiber optic cloth 102 or to a backing on the cloth. A person of ordinary skill in the art will recognize that a number of variations on these described configurations can be used in keeping with the spirit of the invention.

Light applicator 170 is configured in the form of a "patch" that can be applied directly to the skin. In this exemplary embodiment, a backing 172 is provided that is larger than the fiber optic cloth 102 so that an adhesive can be applied on the margin of the backing that faces the skin. In this way, adhesive need not be applied to the skin facing portion of fiber optic cloth 102 as the optical qualities of the cloth may be impacted by the application of such an adhesive. Light is fed to fiber optic cloth 102 in this embodiment by a fiber optic cable 106, which can be connected using connector 108 to a light source 110, which in turn can be powered by an "off-board" energy source if desired using wire 128.

Figure 5:
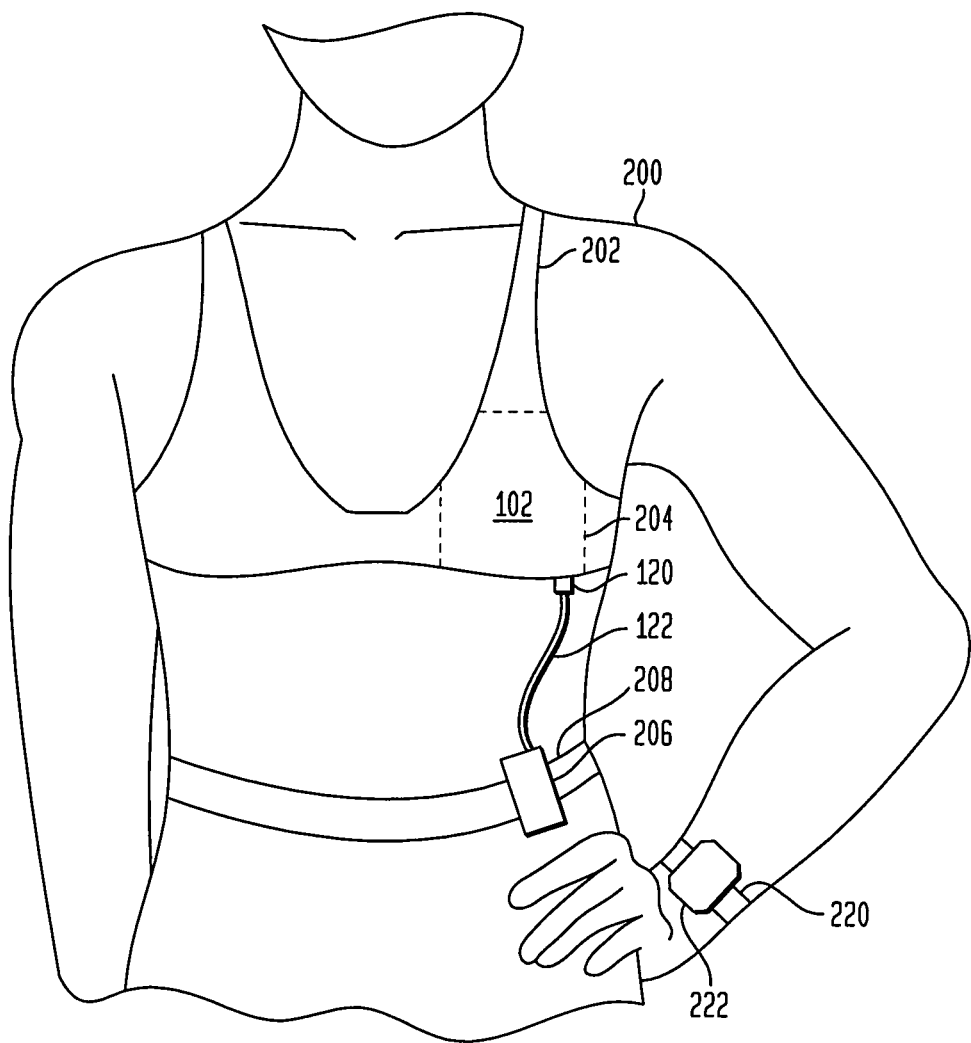
FIG. 5 illustrates two further applications of the light applicator of FIG. 2.

FIG. 5 illustrates the application of two light applicators to a patient 200. In a first application, a fiber optic cloth 102 is built into a patient's clothing, particularly brassiere 202, using stitching 204. In this application, connector 120 allows wire 122 to run to a controller 206 mounted on the patient's belt 208. Controller 206 may include an energy source such as a battery. Controller 206 may also include regulating electronics to process the energy for consumption by the light applicator. Still further, controller 206 may include on/off and/or attenuation controls to allow a particular power level to be set for energy delivery to the light application. Still further, controller 206 may include a processor that allows for a course of treatment to be "programmed"—setting, for example, particular power levels to be provided at particular times and particular durations for the light applicator.

The second application illustrated in FIG. 5 provides a light applicator in the form of a wrist band 220. The wristband may consist entirely of fiber optic cloth, or it may have a skin facing fiber optic cloth with a further fabric covering, or other combinations as may be known to the person of ordinary skill. In this example, a controller 222, similar to controller 206, is mounted directly to the item of clothing (here the wristband).

The invention may be applied to treat a variety of patients, including those having cutaneous, subcutaneous, mucosal, intra-articular and hematologic diseases that may be amenable to treatment using PDT. These patients include, but are not limited to, skin and soft-tissue cancer patients, acne patients, patients with photodamaged skin (such as those with actinic keratoses, dyspigmentation, solar elastosis and including those with wrinkles), patients with breast cancer, in particular metastatic lesions through the dermis/epidermis and subcutaneous and breast fat and certain lymphomas.

One indication that may be particularly appropriate for application of the present invention is the eradication of external lesions where, currently, multiple high dose treatments are completed for conventional PDT to effect treatment. It is possible that continuous low irradiance treatment such as that provided by the present invention will be preferable for long term survival. This strategy eliminates problems associated with high dose treatments, including depletion of tissue oxygen (O2), which is converted to effect tumor kill. The use of continuous low irradiance therapy for external lesions will be increased if patients are minimally inconvenienced during their long term treatment. This suggests that a wearable system may be optimal, whereby the patient can complete normal activities of daily living during treatment. Alternatively or in addition, long term treatment can be achieved during the night while sleeping. The present invention can facilitate long term treatment by providing suitable light exposure in an unobtrusive manner. Patient inconvenience for repeated visits, and excessive thermal damage caused by the high laser powers used. As a result of the disadvantages of conventional PDT, many such lesions are not treated using PDT. A further condition that may be currently undertreated using PDT is the erosion of breast cancer lesions through the dermis and epidermis. This indication, known by clinicians as "field of fire" should be optimal for continuous low irradiance PDT treatment.

The light applicator of the invention can be woven or formed into the appropriate garment such as a ski mask for facial tumors or shirt for chest wall cutaneous metastases from breast cancer or socks for diabetic foot and leg ulcers. Construction of the light applicator can also include the ability to control areas within the garment which receive light of differing intensities or specific wavelengths of light in different portions of the garment or garments, for example by overlapping or weaving side by side fiber optic fibers that are powered by different light sources and/or control electronics. For example, in the treatment of mammary Paget's disease, a fiber-optic brassiere could be fashioned in which a particular wavelength of light emanates over the areolas and a different wavelength of light over the tail of the breast and no light emitted on the posterior portion of the garment. In the treatment of psoriatic arthritis, fiber-optic gloves could be fashioned which emit a higher intensity, short wavelength light on the dorsal aspect of the joint where the skin is thinner and a longer wavelength light on the volar/plantar aspect where skin is thicker and deeper penetration is necessary.

Continuous therapy, outside the physician's office or hospital can also be enabled by such a wearable light-emitting garment. In diseases such as cutaneous T-cell lymphoma, where patients undergo extra-corporial photophoresis, the risks of the blood circuit, infection, blood loss, thermal damage to blood elements, pain and need to be in a hemodialysis unit for the treatment may be eliminated. By simply wearing a shirt and pants garment, 90% of the cutaneous surface, with its vast vascular plexuses will enable these lymphoma patients non-invasive, high-quality of life therapy. Wearable chronic therapy PDT devices will be useful for all external and subcutaneous medical conditions treatable via current and future PDT applications. This includes skin cancers, and other skin conditions, including acne, leg ulcers and proliferative diseases such as actinic keratoses, psoriasis, etc. Due to deeper penetration of longer wavelength light, subcutaneous diseases, such as cancers metastatic to skin/subcutis can be treated, as well as intra-articular diseases in small joints of the hands—psoriatic and rheumatoid arthritis.

Figure 6:
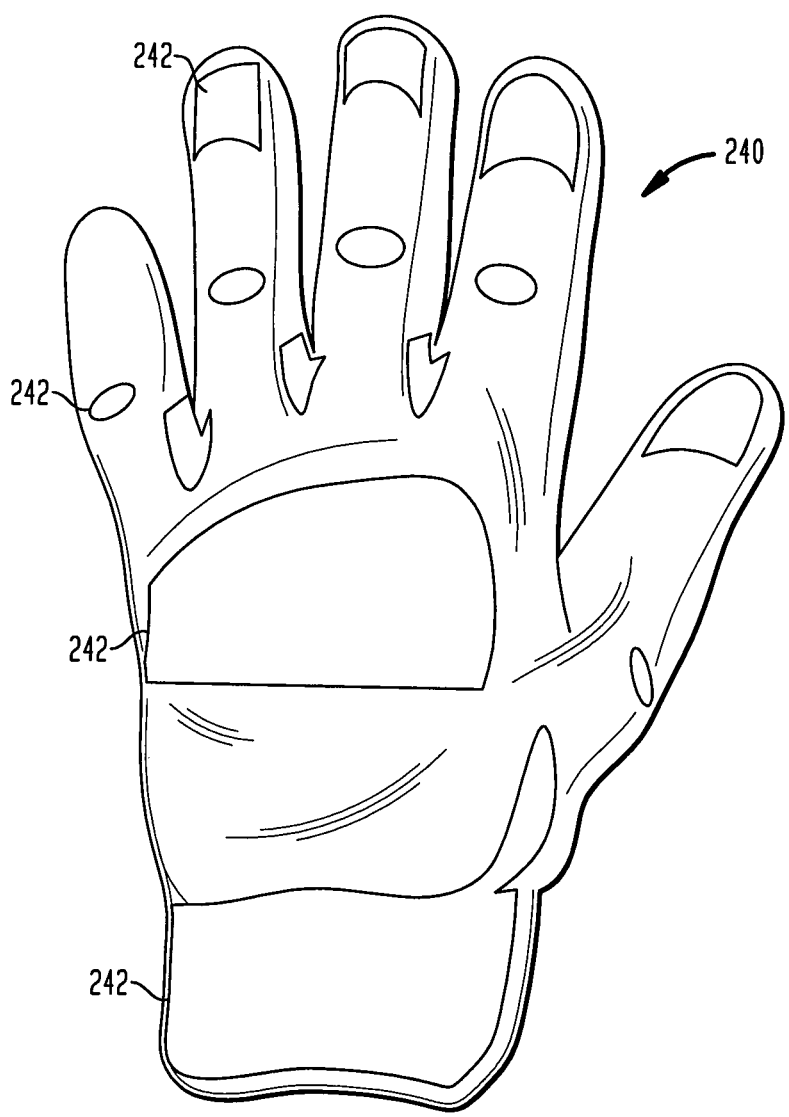
FIG. 6 illustrates a further application of the light applicator of FIG. 2.

By way of example, arthritis and intra-articular diseases in the small joints of the hands could be treated using the glove 240 illustrated in FIG. 6. In this example, a number of light applicators 242 (illustrated in the Figure as black regions) could be integrated into the glove 240 so that the light applicators apply light to the desired joints, such as the distal and proximal interphalangeal joints and metacarpal-phalangeal joint an embodiment for treating arthritis. The palmar surface could also be illuminated for palmoplantar psoriasis. In a further elaboration of this embodiment, fluence could be moderated to each site, or each site turned on and off independently, by a controller located on the glove or connected to it by an appropriate cable or cables (not shown).

In a further specific application of the invention, continuous low irradiance photodynamic therapy can be effective for human subjects with chest wall recurrences of breast cancer and skin metastases of malignant melanoma that have failed conventional ionizing radiation therapy. Chest-wall progression of breast cancer is disproportionately seen among underserved populations and re-treatment of previously of irradiated skin often is problematic in all socioeconomic groups. Conventional photodynamic therapy is reported to have complete response rates of 64-89% for chest-wall progression of breast cancer in patients who have failed radiation, chemotherapy and surgical resection. PDT has not entered mainstream cancer care due to excessive morbidity and the complexity of administering the therapy. Virtually 100% of patients develop skin necrosis and large areas of full-thickness skin ulceration, requiring inpatient management, pain and protracted wound care. These factors limit the size of the treatment field and few Centers offer this therapy. In contrast to conventional photodynamic therapy, which can induce non-specific tissue necrosis, continuous low irradiance photodynamic therapy of the invention may avoid necrosis and the resulting full-thickness skin ulceration. Large cutaneous surfaces, such as the entire chest-wall for breast cancer could then be treated with the invention.

The invention being thus disclosed and illustrative embodiments depicted herein, further variations and modifications of the invention will occur to those skilled in the art. All such variations and modifications are considered to be within the scope of the invention, as defined by the claims appended hereto and equivalents thereof.

What is claimed is:

1. A method for providing continuous low irradiance photodynamic therapy to a patient's cancer, comprising:
   applying a photosensitizer to the patient;
   applying a conformable skin facing light applicator to the patient; and
   providing continuous low irradiance photodynamic therapy of between about 0.25 and 3 mW/cm$^2$ through the light applicator to activate the photosensitizer and thereby treat the patient's cancer.

2. The method of claim 1, wherein the light applicator is applied to the patient continuously for a period of greater than or equal to about four hours.

3. The method of claim 1, wherein the light applicator is applied to the patient continuously for a period of greater than or equal to about 12 hours.

4. The method of claim 1, wherein the light applicator is applied to the patient continuously for a period of greater than or equal to about 24 hours.

5. The method of claim 1, wherein the light applicator has an effective treatment area of greater than or equal to 10 cm$^2$ to thereby provide treatment over an area of greater than or equal to 10 cm$^2$.

6. The method of claim 1, wherein the light applicator has an effective treatment area of greater than or equal to 100 cm$^2$ to thereby provide treatment over an area of greater than or equal to 100 cm$^2$.

7. The method of claim 1, wherein the method is applied to treat chest wall progression of breast cancer in the patient.

8. The method of claim 1, wherein the method is applied to treat skin metastases of a malignant melanoma.

9. The method of claim 1, wherein the method is applied to treat a skin or soft tissue cancer.

10. The method of claim 1, wherein the light applicator includes a fiber optic cloth.

11. The method of claim 10, wherein the light applicator is integrated into a garment worn by the patient.

12. The method of claim 1, wherein applying the photosensitizer comprises applying 5-aminolevulinic acid.

13. The method of claim 12, wherein the photosensitizer is administered orally.

14. The method of claim 1, wherein the light applicator includes two surface areas and the step of applying the applicator to the patient includes applying the two surface areas to two areas of the patient's skin.

15. The method of claim 14, wherein the two surface areas provide light of differing intensity.

16. The method of claim 15, wherein the two surface areas provide light of differing wavelengths.

* * * * *